July 4, 1944. O. NELSON Plant Pat. 633
SANSEVIERIA PLANT
Filed June 24, 1943
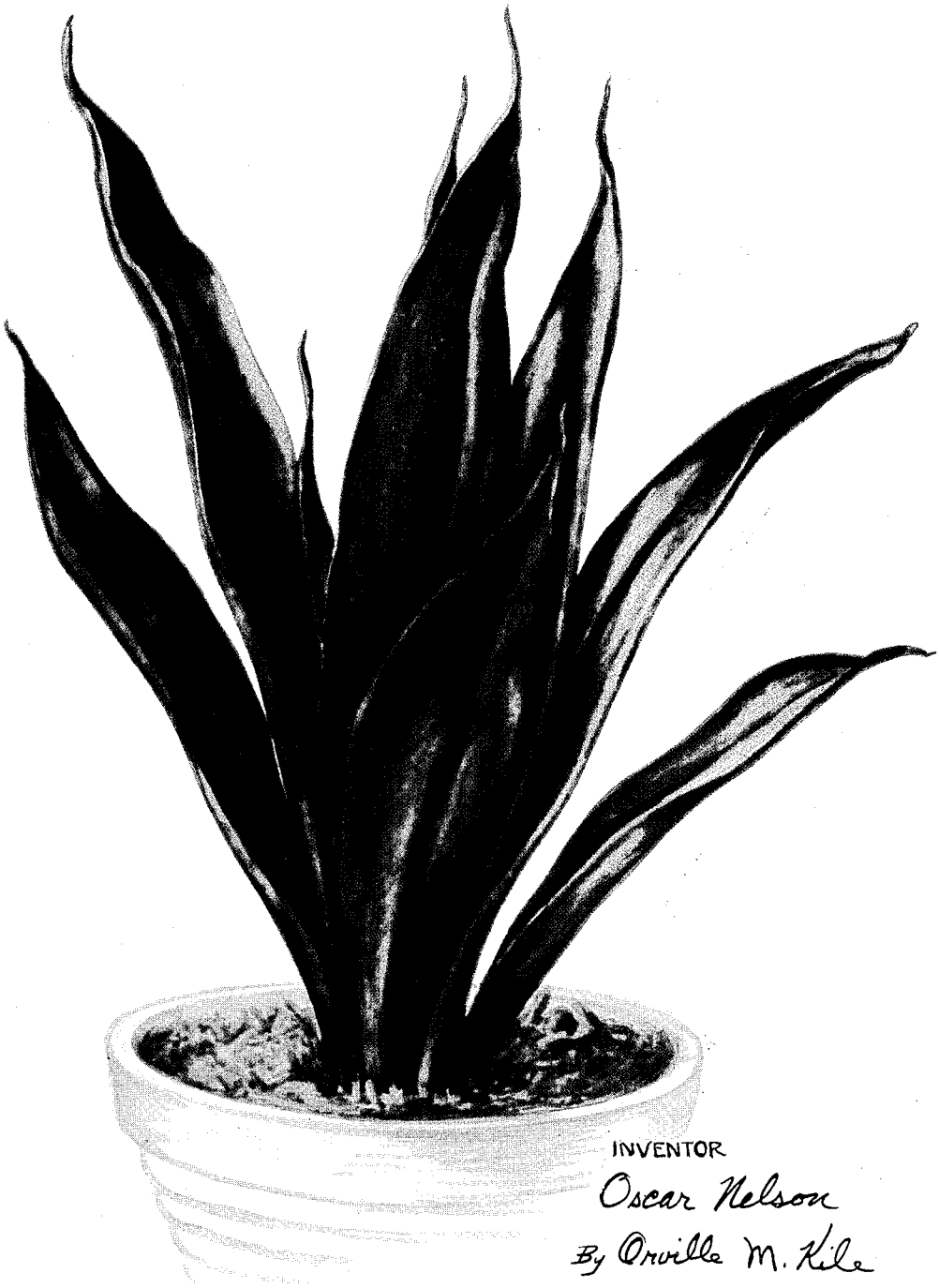
INVENTOR
Oscar Nelson
By Orville M. Kile
PLANT PATENT AGENT Patented July 4, 1944

Plant Pat. 633

UNITED STATES PATENT OFFICE

633

SANSEVIERIA PLANT

Oscar Nelson, Miami, Fla.

Application June 24, 1943, Serial No. 492,082

1 Claim. (Cl. 47—59)

My present invention or discovery relates to an improved variety of Sansevieria in new combination of characteristics, including dwarf and compact growth, dark green color and distinctive reproduction habits for this type of Sansevieria.

My new variety is a second generation sport of Laurentii. It so happened that Laurentii produced at about the same time two sports that were so nearly alike that I could not distinguish them. I discovered one of these sports and bought the other. Since they were apparently identical, I grew them together. It is therefore impossible for me to state which one of these first generation sports of Laurentii was the parent of my present second generation sport which is the new variety herein described.

The principal differences between my new variety and its parent, the original Laurentii sport, are in the color, size, type of growth, and reproduction habits of the two varieties. The original sport reproduces "true" only by means of suckers. But my new variety produces its own kind both by suckers and by leaf cuttings. These characteristics of reproduction, as well as the other characteristics, have proved to be firmly fixed in my new variety.

The growth of this new variety is compact and narrow at the base but spreads at the top. Its leaves are somewhat broader in the center but come to a long, sharp point. Its height under ordinary circumstances is much less than that of Laurentii or of its parent.

The illustration making a part of this specification shows a typical one-year-old plant of my new variety.

Following is a description of the new variety:

Growth:

*Type.*—Semi-dwarf; compact and narrow at base; spreading at top.

*Rapidity.*—Grows very rapidly. Roots readily.

Size.—Average one-year plant is between 6 and 7 inches in height, with a spread of 5 to 6 inches. It may be produced in larger or smaller sizes (from 3 to 10 inches in height), depending upon the technique used in propagating it.

Leaves:

*Shape.*—Long; narrow at base; top narrow and with long slender points. Central portion somewhat wider. Almost flat but with slight depression or trough in center. Margin entire and straight.

*Size.*—Most of the leaves on a plant are pretty much the same length. The average one-year plant has some leaves which are an inch or more in width at their centers.

*Colors.*—Dark velvety green—between Empire Green (Plate xxxii, Ridgway) and Dull Blackish Green (Plate xli).

*Texture.*—Smooth and substantial.

*Quantity.*—More leaves per plant are produced than is usual with Sansevierias.

Flowers: No flowers or fruit have been known to appear.

Reproduction: Asexual, both by suckers and leaf cuttings.

*Comparison*

The variety most like my new variety is its parent, an unnamed sport of Laurentii. The principal differences between these two varieties are enumerated below:

1. The leaves of my new variety are a dark velvety green color with no variegation, while its parent has leaves which are a somewhat lighter green with a yellow margin.

2. The leaves of my new variety are somewhat narrower and more "streamlined" than those of its parent.

3. The leaves of my new variety are not as inclined to be "wavy" as those of the parent plant.

4. My new variety is more inclined to dwarf growth, its height being from 3 to 10 inches, while its parent grows from 6 to 18 inches high.

5. My new variety has a more compact growth.

6. My new variety averages more leaves to the plant.

7. My new variety reproduces "true" from both suckers and leaf cuttings, while the parent variety produces "true" only by means of suckers.

Having thus disclosed my discovery, I claim:

The new and distinct variety of Sansevieria plant having the novel combination of features shown and described, characterized particularly by its semi-drawf and compact growth; its smooth, velvety dark green leaves; and its ability to reproduce true by means of both suckers and leaf cuttings.

OSCAR NELSON.